United States Patent [19]

Liegner

[11] Patent Number: 4,459,984
[45] Date of Patent: Jul. 17, 1984

[54] SPEAKING TRACHEOSTOMY TUBE

[76] Inventor: Kenneth B. Liegner, 315 Bear Ridge Rd., Pleasantville, N.Y. 10570

[21] Appl. No.: 418,407

[22] Filed: Sep. 15, 1982

[51] Int. Cl.³ .......................................... A61M 16/00
[52] U.S. Cl. ........................... 128/207.15; 128/207.16
[58] Field of Search ...................... 128/207.15, 207.14, 128/200.26, 207.17

[56] References Cited
U.S. PATENT DOCUMENTS 3,659,612  5/1972  Shiley et al. .................. 128/207.15
4,280,492  7/1981  Latham ........................... 128/207.15

FOREIGN PATENT DOCUMENTS 1040425  8/1966  United Kingdom .......... 128/207.15

Primary Examiner—Henry J. Recla
Attorney, Agent, or Firm—Kane, Dalsimer, Kane, Sullivan and Kurucz

[57] ABSTRACT

The disclosure is of a tracheostomy tube for partial insertion into the trachea of a human, for the purpose of providing an airway from outside of the human's body directly into the trachea. The tracheostomy tube of the invention provides a controlled air leak to the upper trachea, whereby the patient may speak during mechanical ventilation.

6 Claims, 11 Drawing Figures

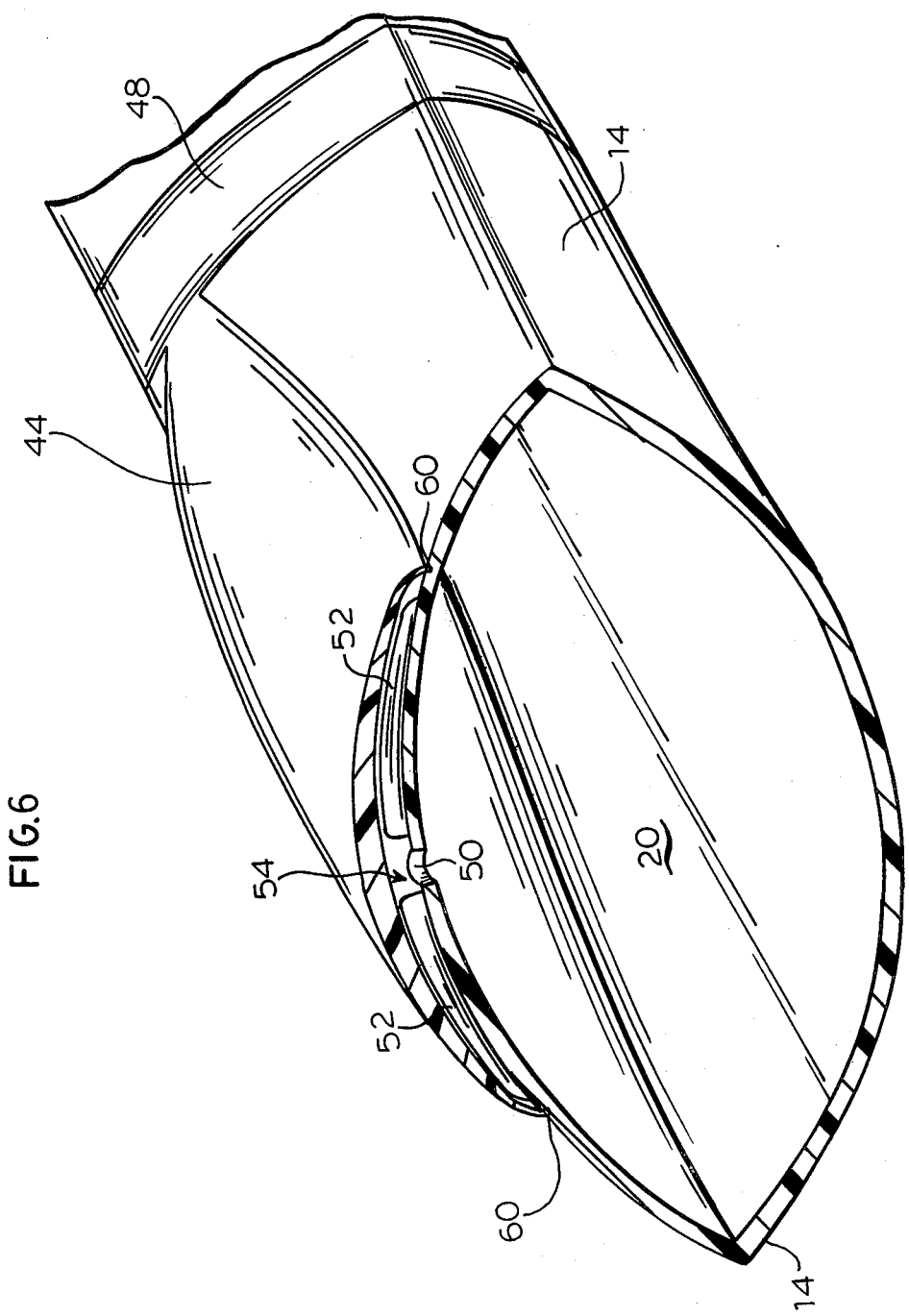

SPEAKING TRACHEOSTOMY TUBE

BACKGROUND OF THE INVENTION

1. Field of the Invention

The invention relates to surgical appliances and more particularly relates to a tracheostomy tube.

2. Brief Description of the Prior Art

Humans suffering from respiratory failures may on occasion require tracheostomy and mechanical ventilation for variable periods of time, including very extended periods. In general, this situation makes speech impossible and such patients are required to communicate by means of writing. This is often physically awkward or impossible with poor legibility or illegibility and is unsatisfactory for fluent, spontaneous communication. On the other hand, patients may silently mouth the words they wish to speak, relying on others' lip reading ability to be understood. This may be the only alternative for some, for example quadraplegic patients who cannot write and who are left with only diaphragmatic breathing. In any case, these patients and those who care for them are often left frustrated and depressed, powerless to communicate effectively. Furthermore, the absence of speech in these patients, sometimes for many months or years may serve to depersonalize and dehumanize them in the eyes of some, fostering their treatment as mere objects rather than as subjects for empathic concern, caring, and communication.

Many different types of tracheostomy tubes exist. Most are expressly designed to block passage of air from the lumen of the tube to the upper airways or around the cuff which surrounds the tube near its distal end, producing an airtight seal with the wall of the trachea (when inflated). Some types of tracheostomy tubes permit patients, at a time they are no longer totally ventillator dependent, to talk by means of plugging the tracheostomy stoma while either a "fenestrated" tracheostomy tube is in place or the cuff is deflated. These maneuvers allow a flow of air from the lower tracheo-bronchial tree to exit through the tube (in the case of a fenestrated tube) or around the tube (in the case of cuff deflation) and between the patients vocal cords and upper airways thereby permitting phonation and vocalization. For these types of tubes to be utilized successfully, however, the patient must be capable of inhaling and exhaling effectively on his own.

Only one type of currently existing tracheostomy tube permits vocalization during mechanical ventilation. This is the so-called "Pitt Tube". This tracheostomy tube makes use of a separate tiny catheter running in a channel in the wall of the tracheostomy tube which opens on the cephalo-dorsal aspect of the tracheostomy tube just proximal to the cuff. The external end of the catheter is fitted with an adaptor to which a source of pressurized gas may be connected. Thus connected, a jet of gas exits the opening cephalo-dorsal on the tracheostomy tube and above the cuff, flowing cephalad between the vocal cords and permitting vocalization. A separate source of pressurized and desirably humidified and warmed gas must be provided. The patient is required to control the flow of gas by manipulating a flow regulating value. Although the Pitt Tube provides a great achievement in granting tracheostomized mechanically ventillated patients the gift of speech, it does entail certain disadvantages.

First, since the device requires a second source of pressurized and desirably humidified and warmed gas (usually an air/oxygen mixture), there may be a problem in its operation. Many if not most hospital rooms including intensive care unit modules are designed with only one oxygen source per patient. If this gas source is connected to the ventilator, then special arrangements must be made to provide a gas source for the catheter leading to the "air jet" which makes vocalization possible with the Pitt Tube. Cumbersome cylinders of pressurized gas might need to be brought in proximity to the patient. In addition, additional oxygen/air blenders, humidifier, and warmer are needed to treat the cephalad flowing gas to prevent damage to the tracheal mucosa and vocal cords. These impediments serve to discourage the widespread use of the device, to the detriment of patients who otherwise would benefit from it. These problems are all circumvented in the present invention because the warmed, pressurized, humidified oxygen/air mixture flowing from the ventillator itself would at once provide both caudad flow of air to the lower airways to ventilate the patient and a cephalad stream of air to permit vocalization. Thus the complex, costly, and ingenious components already incorporated in the ventilator could be used to best advantage without the need for redundant and cumbersome gas source, humidifier, warmer, and pressurizer.

It is also a disadvantage where the patient is required to regulate a flow of gas as described above. The present invention does not require any manual or physical manipulation by the patient. Thus it could be readily utilized even by quadraplegic patients or patients with advanced debilitating neurological diseases.

Another disadvantage of the prior art device resides in its special design, which is somewhat limiting because of its relative complexity. The orifice and valve of the talking tracheostomy device of the invention could be incorporated into nearly all types of standard tracheostomy tubes to provide a controlled air leak permitting speech in the mechanically ventilated patient yet guarding the lower airways against aspiration. Its essential simplicity should encourage its widespread utilization, hopefully to the benefit of the many tracheostomized, mechanically ventilated patients currently denied the humanizing trait of speech.

An additional advantage of the device of the invention is that the flow of air available for vocalization is cyclical, resembling (although with reversed phase) the naturally occurring events in spontaneous speech. With time patients can adapt themselves more easily to the phasic flow of air produced by the ventilator cycle via the orifice valve. In addition, patients would be able to utilize to at least some degree their own remaining neuro/musculo/skeletal respiratory function to influence airway pressures and hence flow rate via the orifice valve. Thus they can exert some degree of control over modulation, accentuation, emphasis, and timing of their own speech, unlike the Pitt tube wherein flow is either absent or present (with little modulaton possible) depending on whether the flow control valve is manually turned on or off.

SUMMARY OF THE INVENTION

The invention comprises a tracheostomy tube for partial insertion into the trachea of a human for the purpose of providing an airway from outside of the human's body, directly into the trachea, which comprises;

1. a curved cannula having (a) a first open end;
(b) a second open end;
(c) a cannula body between and joining the first and second open ends;
(d) a lumen providing open communication between the first and second open ends; said cannula body (c) having
  (i) a stoma zone adjacent the first open end; and
  (ii) a trachea zone adjacent the second open end; said body being adapted by size and configuration to be inserted and positioned in a stoma sited in the neck of the human so that the first end is outside of the human's body, the stoma zone of the body is within said stoma, the trachea zone and the second end of the body are in said trachea; and
(e) an aperture in the trachea zone of the cannula body, providing open communication between the cannula lumen and the trachea at a point between the second open end and the stoma zone of the cannula body;
2. means adjacent the second end, connected to the trachea zone of the cannula body, for forming a gas seal between the cannula body and the trachea walls when the cannula is positioned in said trachea; and
3. valve means associated with said aperture, for permitting gaseous flow through the aperture, while preventing debris from entering the cannula lumen via the aperture.

BRIEF DESCRIPTION OF THE DRAWINGS

FIG. 6 is a view along lines 6—6 of FIG. 3 with the valve member or cover in place.

DETAILED DESCRIPTION OF THE PREFERRED EMBODIMENTS OF THE INVENTION

Those skilled in the art will gain an appreciation of the invention from a viewing of the accompanying FIGS. 1 through 13, inclusive, accompanied by a reading of the following description of the preferred embodiments.

Figure 1:
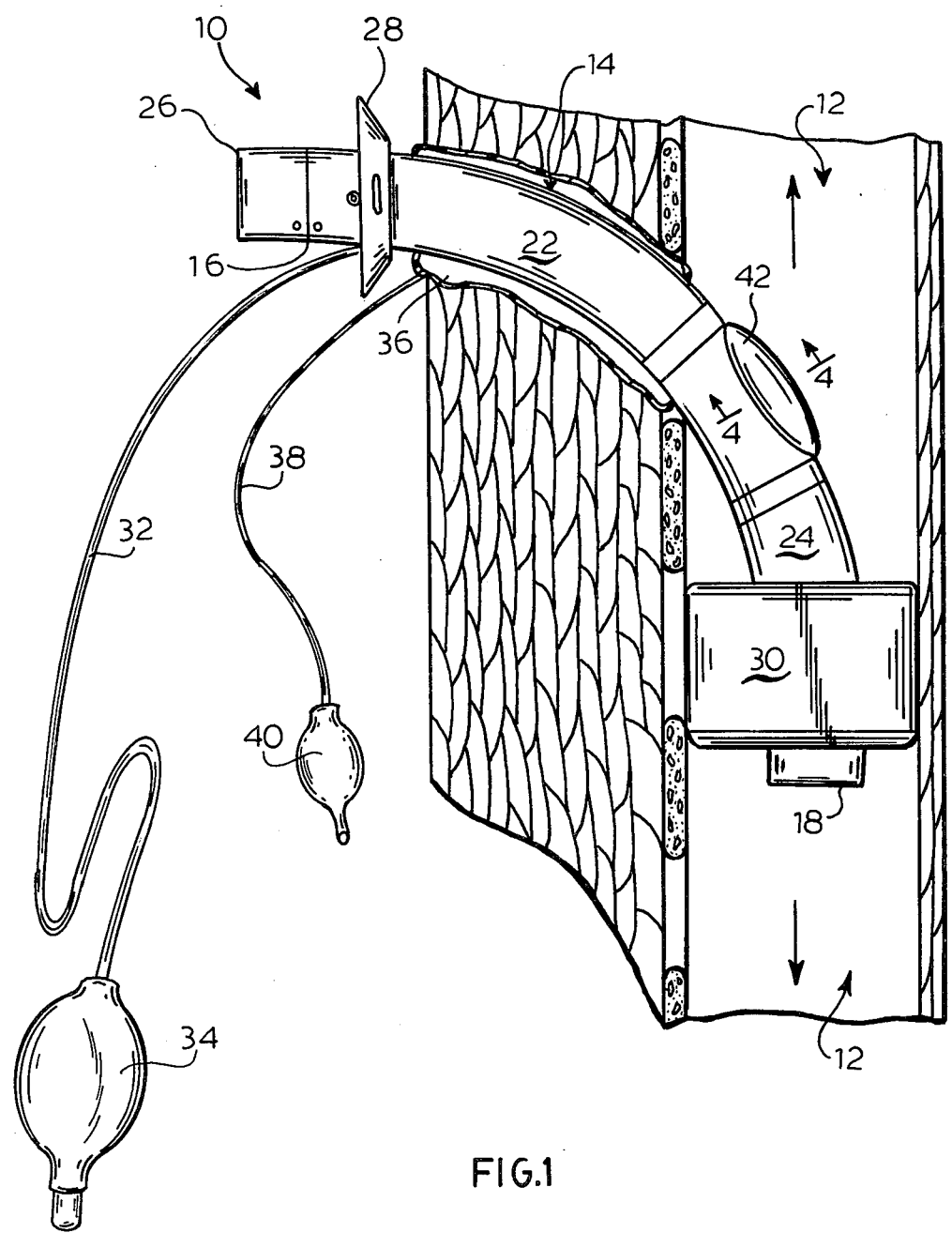
FIG. 1 is a side view of an embodiment tracheostomy tube of the invention, shown in place during use.

Referring first to FIG. 1, there is seen a side view of an embodiment tracheostomy tube of the invention, shown in place in the throat region of a human. The tracheostomy tube 10 of the invention is shown partially inserted into the trachea 12 of the human, for the purpose of providing an airway from outside of the human's body directly into the trachea 12. The tracheostomy tube 10 of the invention comprises a curved cannula 14 having first open end 16 and a second open end 18. The cannula 14 has a body between and joining ends 16, 18. A lumen 20 (not seen in FIG. 1; see FIG. 4) provides open communication between the ends 16, 18. The body of the cannula 14 comprises a "stoma" zone 22 adjacent the first open end 16 and a "trachea" zone 24 adjacent to the second open end 18. The terms "stoma zone" and "trachea zone" refer to the positions of the cannula body portions when inserted into the trachea of a human patient, as depicted in FIG. 1. The body of the cannula 14 is adapted by size and configuration to be inserted in position in a stoma sited in the neck of the human so that the first end 16 is outside of the human's body and the trachea zone 24 together with second end 18 are in the trachea of the human patient.

In the embodiment tracheostomy tube 10, an inner cannula 26 has been inserted into the lumen 20 through the open end 16 where it is locked in place. An inner cannula 26 is not a necessary component for a tracheostomy tube 10 of the invention but may be part thereof as a preferred embodiment as will be described hereinafter. Inner cannulas are frequently found in prior art tracheostomy tubes, and function to facilitate cleaning of the device, i.e.; the inner cannula may be removed and cleared of debris while the outer cannula remains in place. After cleaning it can be replaced within the outer cannula. The inner cannula 26 should have an orifice in the body thereof (not shown in FIG. 1), matching and corresponding to the orifice 50 described hereinafter. As also shown in FIG. 1, the tube 10 of the invention has an annular flange 28 around the cannula 14 body to stabilize the tube 10 when it is positioned, by providing a means to secure the tube 10 to the patient's skin surface. A cuff 30 is annularly disposed about the cannula 14 body in the tracheal zone 24. The cuff 30 is an inflatable cuff which functions as a means adjacent the end 18 to form a gas seal between the cannula body 14 and the tracheal walls of the patient, when the cannula is positioned in the trachea as shown in FIG. 1. The cuff 30 is inflated by means of a connecting tube 32 and the associated pilot balloon pump 34 which functions to inflate or deflate a cuff 30 with air. Although not necessary to the device of the invention, it may be desirable for a second cuff 36 to be positioned annularly about the cannula body 14 in the stoma zone 22 to provide a means for a gas seal between the cannular body 14 and the stoma sited in the patient's throat area. Cuff 36 is, like cuff 30, inflatable and deflatable through the connected tube 38 and the associated pilot balloon pump 40.

The tracheostomy tube 10 as described above, is actually representative of many prior art tracheostomy tubes, with the exception of the presence of a cuff 36 in the stoma zone 22. The latter structure is considered to be in itself novel.

A further novel structure in tube 10 is found in the flap valve 42 positioned on the stoma zone 24 area of the cannular body 14.

Figure 2:
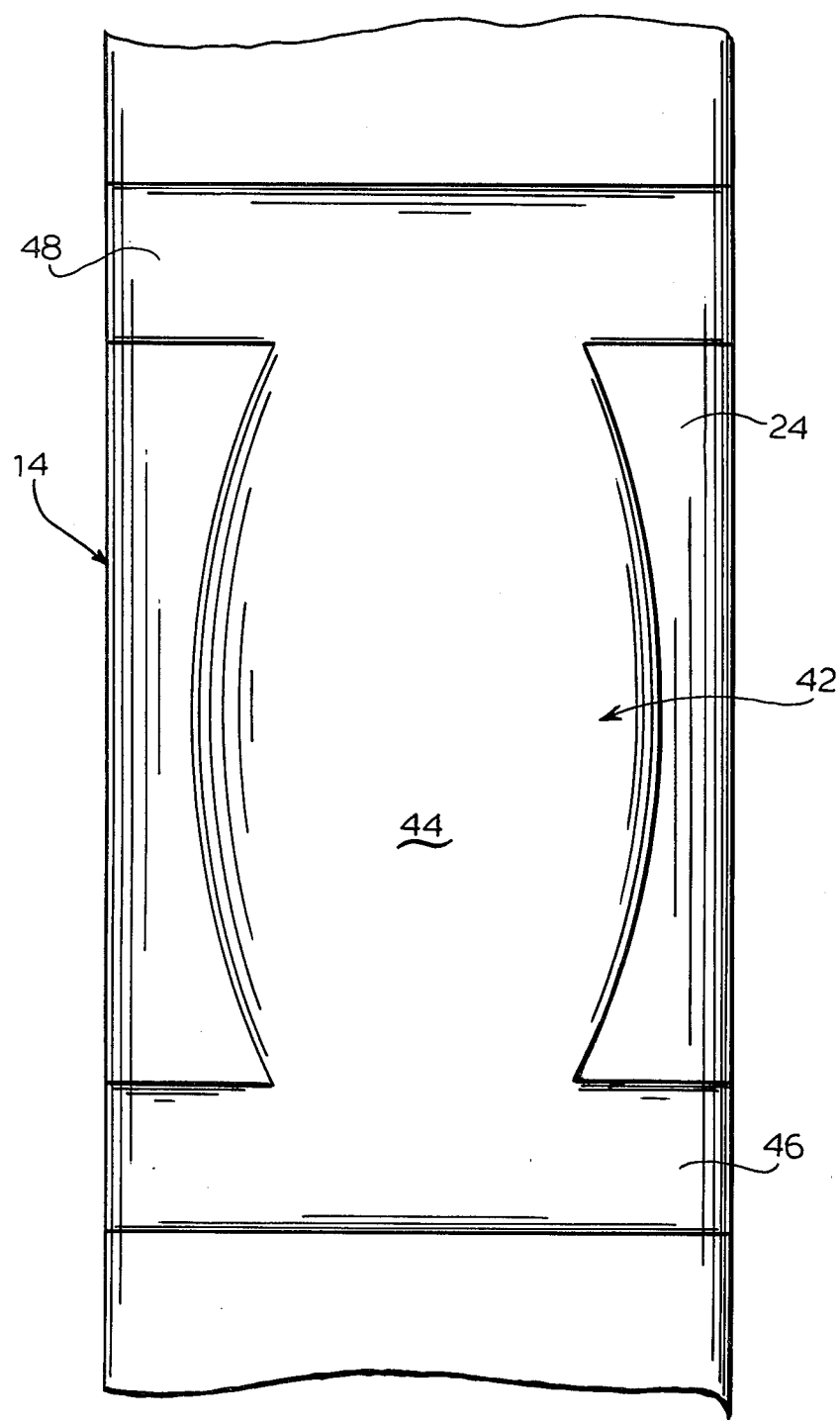
FIG. 2 is a top view of a portion of the embodiment tube shown in FIG. 1, at the valve site.

Referring now to FIG. 2, there is seen an enlarged, top view of a portion of the embodiment tube 10 shown in FIG. 1, at the flap valve 42 site. The flap valve 42 includes a resilient, moving valve member 44 secured at each end to the cannula body 14 by integrally molded bands 46 and 48. Bands 46,48 circumscribe the cannula body 14 as a means of attachment thereto. In preferred embodiment tubes 10 of the invention, the bands 46,48 are secured adhesively to the cannula body 14 to prevent lateral displacement of the flap valve 42 from its desired position on the cannula body 14. The flap valve 42 is preferably formed of a premolded, flexible, yet shape-retaining material, such as an elastic, synthetic, polymeric resin. Alternatively, a natural rubber material would be satisfactory.

Figure 3:
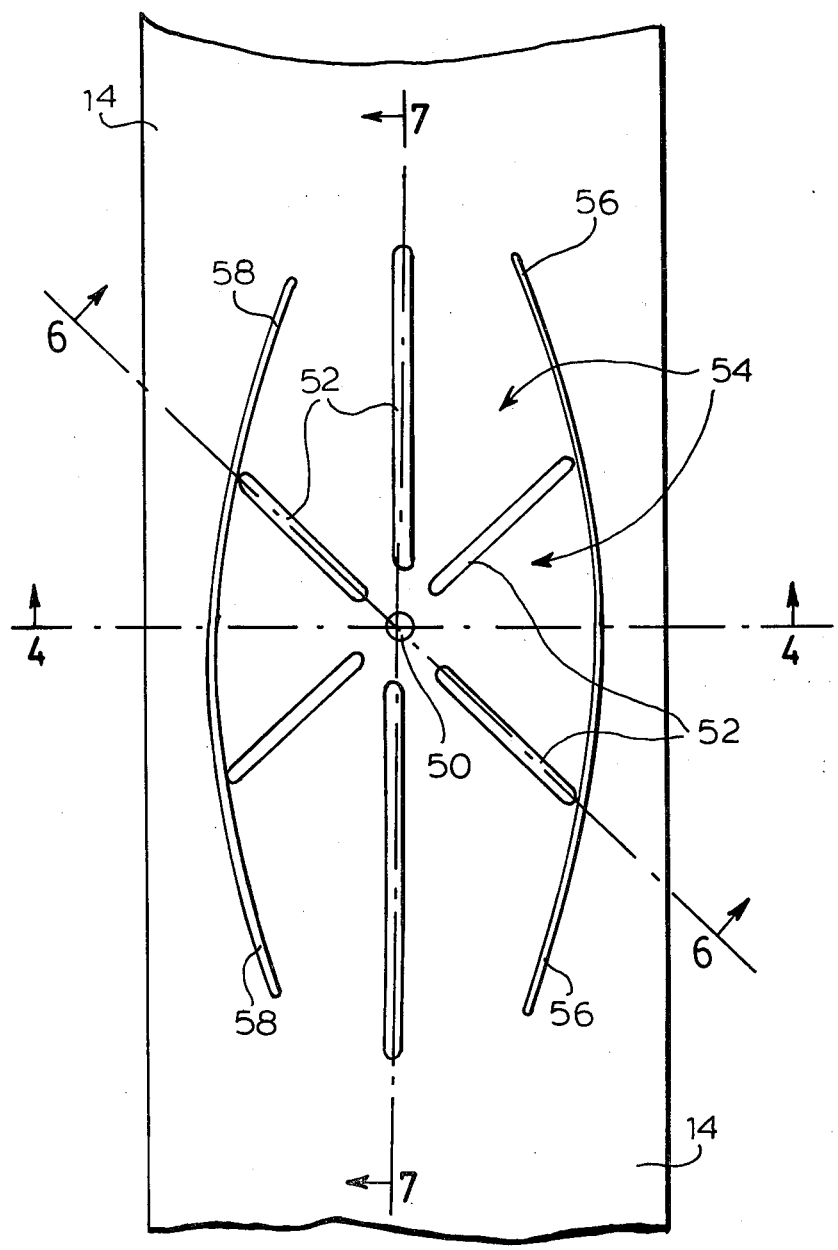
FIG. 3 is a view as in FIG. 2, of the underlying valve mechanism.

The valve member 44 has been removed in the drawing of FIG. 3 to show the underlying flap valve 42 mechanism. As seen in FIG. 3, at approximately a central point underneath the valve member 44 there is an orifice or aperture 50 which pierces the cannula body 14 to provide communication between lumen 20 and the trachea (when tube 10 is inserted into a trachea of a human) at a point between the open ends 16, 18 of the cannula body 14. Radially disposed about the orifice 50 are a plurality of raised ribs or struts 52. The struts 52 function to hold valve member 44 off the surface of the cannula body 14 except at the forward ends integrated with bands 46, 48. There is thus a space 54 beneath valve member 44. Along the lateral edges of the valve member 44 there are grooves 56,58 at the marginal boundaries of the flap member 44. These grooves 56,58 on the surface of cannula body 14 serve to receive and hold (frictional engagement) a rib 60 along each peripheral edge of the valve member 44.

Figure 4:
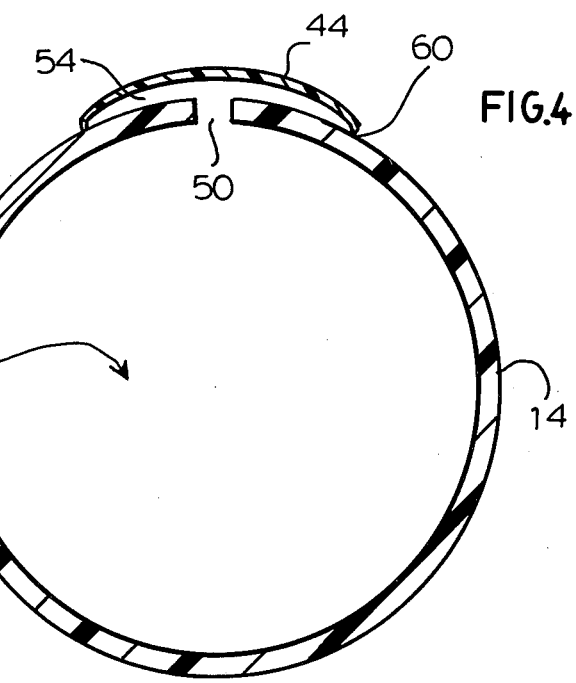
FIG. 4 is a cross-sectional view along lines 4—4 of FIG. 1.
Figure 5:
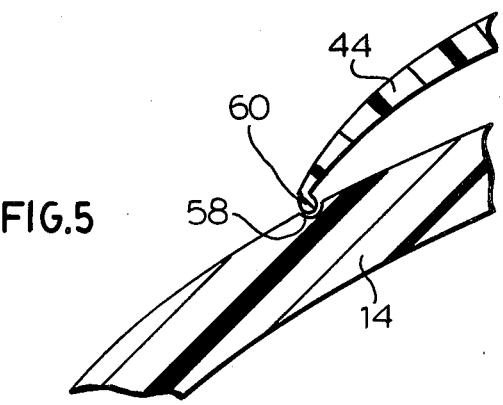
FIG. 5 is an exploded view of a portion of the view seen in FIG. 4.

FIG. 4 is a cross sectional view along lines 4—4 of FIG. 1 and shows in further detail the structure of flap valve 42 including the attachment of flap valve member 44 to the grooves 56,58 through the laterally attached ribs 60. FIG. 5 is an exploded view of a portion of the view seen in FIG. 4 and shows in greater detail the latter construction by which valve member 44 is secured to the cannulaa body 14; see also FIG. 6 which is a view along lines 6—6 of FIG. 3 with the valve member 44 or cover in place.

Figure 7:
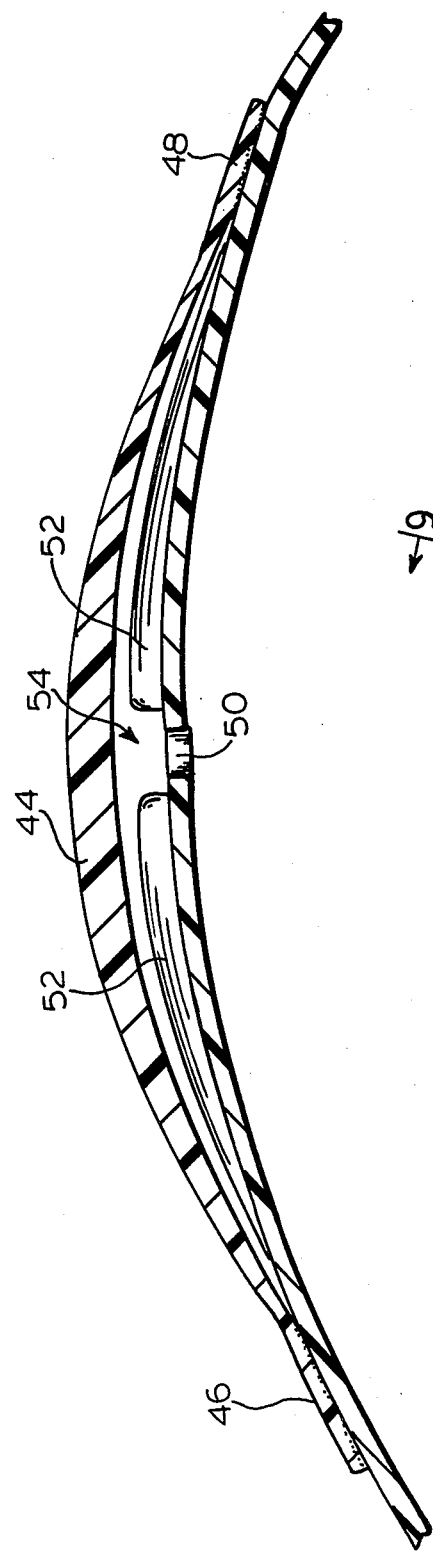
FIG. 7 is a view along lines 7—7 of FIG. 3.

FIG. 7 is a view along lines 7—7 of FIG. 3 and again shows further details of the construction of flap valve 42.

Those skilled in the art will appreciate that the above described tracheostomy tube 10 comprises an otherwise conventional tracheostomy tube, modified in that there is a small orifice 50, guarded by a one way flap valve 42 on the cephalo-dorsal aspect thereof. The orifice 50 and associated flap valve 42 are situated on that portion of the tube 10 which faces cephalad within the trachea 12, towards the vocal cords and upper airways. The orifice 50, which is preferably possessive of a diameter between 1 and 2 millimeters, produces, in effect, a controlled air leak which provides a stream of air passing between the vocal cords and towards the mouth of the patient, permitting patients to phonate and vocalize, even during mechanical ventilation.

The tube 10 of the invention is inserted into the stoma of the patient in a conventional manner and cuff 30 (also 36 if one is present) inflated to seal the trachea 12 at the point of insertion. The open end 16 may be connected to mechanical ventilation equipment in a conventional manner. During operation, a small portion of the air traveling through lumen 20 is forced out of the orifice 50 via a matching orifice in the inner cannula 26 when said inner cannula 26 is present and into the space 54. As the pressure of the air permits, it exits at the ribbed 60 edge of the flap valve member 44. The force of the escaping air raises the edge of the flap member 44 to the degree necessary to permit escape to the upper airways within trachea 12. The generation of negative distal airway pressure, for example by active inhalation by the patient, leads to occlusive apposition of the edges of the flap valve member 44, to the outer surface of the tracheostomy tube 10 body 14, preventing ingress of debris from the upper airways into the distal tracheal-bronchial tree.

From the drawings, it is obvious that the flap valve 42 produces a gently rounded prominence only a few millimeters above the contour of the tracheostomy tube 10 itself. Thus, insertion and/or removal of the tube 10 in no way impedes standard surgical performance of tracheostomy in order to accomodate the device.

The purpose of space 54 beneath valve member 44 is to prevent inspissated secretions from sealing the flap valve member 44 to the surface of the tracheostomy tube 10 body 14, by clogging or by capillary action, which otherwise might occur. In patients with copious secretions, particularly with acute or chronic infections, it is conceivable that even the breathing space 54 might become clogged with secretions. In that case it would be necessary to temporarily remove the tracheostomy tube 10 from the patient and using sterile technique pry the edges of the flap valve member 44 away from the outer surface of the tracheostomy tube 10 body 14 and mechanically, or with irrigation, cleanse debris from the breathing space 54. The tube could then be reinserted in the patient. Alternatively, a completely new tracheostomy tube 10 could be inserted whenever the breathing space 54 becomes clogged with secretions.

Recognition of clogging of the orifice 50 or space 54 beneath the flap valve member 44 is possible by observing the inability of the patient to vocalize voluntarily and by an increase in the measured exhaled tidal volume and minute volume.

As previously described, an inner cannula 26 may be employed in conjunction with the tracheostomy tube 10 as a means of maintaining a clear airway. The inner cannula 26 may have an orifice therein, matching the orifice or aperture 50 in the body 14 of tube 10. However, should the patient find that the constant caphalad flow of air via the aperture 50, and through the flap valve 42 is annoying or disturbing (for example when vocalization is not desired as during sleep), a conventional inner cannula lacking the corresponding orifice matching aperture 50 may be inserted within the lumen 20 of the tube 10. This would act to block the flow of air, stopping the controlled air leak.

Figure 9:
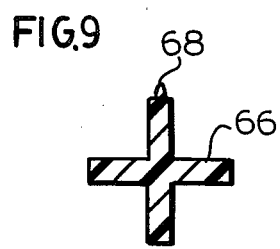
FIG. 9 is a view along lines 9—9 of FIG. 8.
Figure 10:
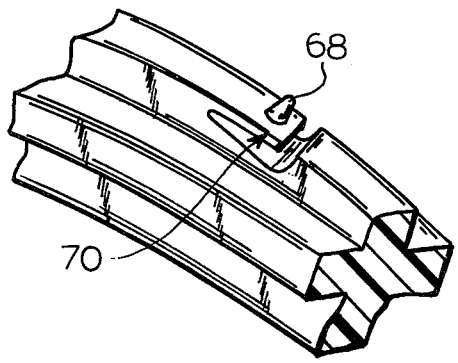
FIG. 10 is an exploded view of a portion of the obturator shown in FIG. 8.
Figure 8:
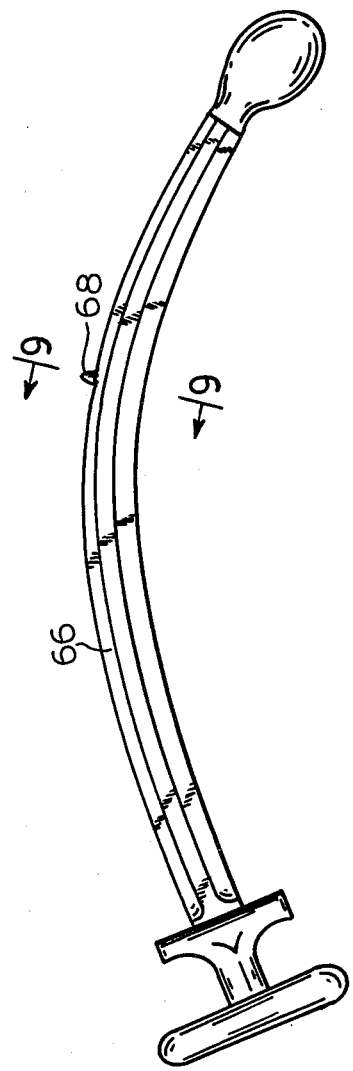
FIG. 8 is a view in perspective of an obturator for use with the embodiment tube of FIG. 1.
Figure 11:
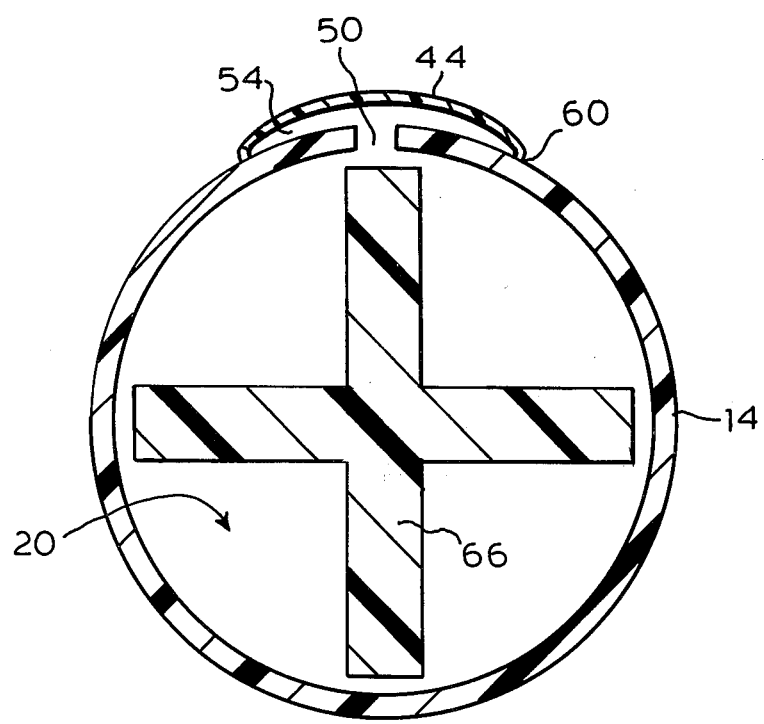
FIG. 11 is a view as in FIG. 4 but with an obturator inserted in the lumen of the embodiment tube.

It will be appreciated that most tracheostomy tubes are supplied by the manufacturers with an accompanying obturator, which aids in the initial insertion of the tracheostomy tube into the patient's trachea. Following insertion, the obturator is removed. Considering that it is conceivable that the orifice or aperture 50 in the tube 10 may become clogged with inspissated secretions, it may be advantageous to provide an obturator with a tiny "side-obturator". Referring now to FIG. 8, such an obturator 66 may be seen. The obturator 66 has a cross sectional configuration as shown in FIG. 9. In general, obturator 66 is a conventional design for an obturator, with the exception that a tiny side obturator 68 has been integrally molded on one surface thereof. When the obturator 66 is fully engaged within tracheostomy tube 10, the side obturator 68 seats within the orifice 50, thus dislodging any obstructing secretions. FIG. 10 is an exploded view of the obturator 68 site on obturator 66 and shows a preferred embodiment wherein obturator 68 sits on a springy flange 70. Thus, when initially inserted into the tracheostomy tube 10, the side obturator 68 will depress into the space beneath springy flange 7 until it reaches the orifice 50. The tiny side obturator 68 will thereupon release to click into place in the orifice 50 when the obturator 66 is fully engaged therein. The side obturator 68 will slide out of the orifice 50 as the obturator 66 is withdrawn, again being depressed into the space beneath the flange 70. In this manner, the orifice 50 can be declogged without having to remove the entire tracheostomy tube 10 from the patient. The inner cannula with its corresponding orifice matching aperture 50 could, of course, be removed for cleansing at any time.

Those skilled in the art will appreciate that the volume and velocity of the stream of air flowing through orifice 50 during operation of the tracheostomy tube 10, would vary depending on the phase of ventilation as well as the mode of ventilation and would be proportional to the pressure generated during each instant of the ventilatory cycle. In volume cycle ventilators the flow through the orifice 50 would be greatest during inhalation when pressures are highest and speech would be most feasible during mechanical ventilatory inhalation (contrary to speech during exhalation normally). On the other hand, the addition of positive end expiratory pressure (PEEP) or continuous positive airway pressure (CPAP) would produce a pressure gradient during all phases of ventilation and should theoretically permit speech during inhalation and exhalation during mechanical ventilation.

The controlled air leak via orifice 50 and valve 42 may be anticipated by the professional staff in choosing ventilator settings for a given patient. Thus, tidal, volume and minute volume may be adjusted upwards to compensate for the volume of the air leak to insure the patient receives the desired actual ventilation. This may be readily achieved and monitored with ventilators such as the Bournes Bear 1, by increasing the tidal volume setting until the measured exhaust volume equals the desired tidal volume (that is, the tidal volume which would have sufficed if there were no controlled air leak). Also, the low exhaled volume alarm would need to be adjusted to reflect the desired exhaled volume rather than the dialed in (nominal) tidal volume. Likewise, the desired level of PEEP or CPAP could be achieved by empirically injusting the PEEP/CPAP dial until the measured proximal airway pressure reaches that level, the air leak notwithstanding.

Those skilled in the art will appreciate that the orifice 50/flap valve 42 described above and drawn in the figures is but one specific means for controlling the gaseous flow through aperture 50. Other types of valves are possible to accomplish the same result. The invention therefore provides a widely applicable means by which tracheostomized mechanically ventilated patients are enabled to talk without impediment. The quality of speech permissible may not be completely normal, as would be expected due to the lack of modulation produced by normal spontaneous breathing. However, the speech obtained should be intelligible and satisfactory.

What is claimed:

1. A tracheostomy tube for partial insertion into the trachea of a human for the purpose of providing an airway from outside of the human's body, directly into the trachea, which comprises;
    a curved cannula having
    (a) a first open end;
    (b) a second open end;
    (c) a cannula body between and joining the first and second open ends;
    (d) a lumen providing open communication between the first and second open ends; said cannula body (c) having
        (i) a stoma zone adjacent the first open end; and
        (ii) a trachea zone adjacent the second open end; said body being adapted by size and configuration to be inserted and positioned in a stoma sited in the neck of the human so that the first end is outside of the human's body, the stoma zone of the body is within said stoma, the trachea zone and the second end of the body are in said trachea; and
    (e) an aperture in the trachea zone of the cannula body, providing open communication between the cannula lumen and the trachea at a point between the second open end and the stoma zone of the cannula body;
    (f) means between the second end and the aperture, connected to the trachea zone of the cannula body, for forming a gas seal between the cannula body and the trachea walls when the cannula is positioned in said trachea; and
    (g) valve means associated with said aperture, for permitting only one-way gaseous flow from said cannula lumen through the aperture during all phases of ventillation, while preventing debris from entering the cannula lumen via the aperture.

2. The tube of claim 1 wherein there is additionally a means adjacent the first end and connected to the stoma zone of the cannula body, for forming a gas seal between the cannula body and the stoma when the cannula is positioned in said trachea.

3. The tube of claim 1 wherein the means for forming a gas seal comprises an inflatable cuff.

4. The tube of claim 1 wherein the valve means comprises a flap valve.

5. The tube of claim 1 wherein there is an obturator positioned within the lumen of the cannula.

6. The tube of claim 5 wherein said obturator includes a means for clearing debris from the aperture.

* * * * *